United States Patent [19]

Gross

[11] Patent Number: 4,746,215

[45] Date of Patent: May 24, 1988

[54] PARTICLE COUNTER AIR INLET ASSEMBLY

[75] Inventor: Kenneth P. Gross, San Carlos, Calif.

[73] Assignee: Pacific Scientific Company, Anaheim, Calif.

[21] Appl. No.: 855,808

[22] Filed: Apr. 24, 1986

[51] Int. Cl.$^4$ .................. G01N 21/05; G01N 21/53
[52] U.S. Cl. .................................... 356/339; 250/576; 356/246
[58] Field of Search ............... 356/338, 339, 438, 439, 356/440, 246; 250/564, 574, 576; 377/10, 53; 340/630

[56] References Cited

U.S. PATENT DOCUMENTS 2,535,181  12/1950  Way .
3,766,489  10/1973  Rosenberg et al. .
3,840,304  10/1974  Hirafaji ........................... 356/246 X
3,893,766  7/1975   Hogg ............................... 250/574 X
4,343,551  8/1982   Eisent .
4,571,079  2/1986   Knollenberg .

OTHER PUBLICATIONS

Royco Instruments drawing 401–7095, initially drawn on Jun. 5, 1969.
Royco Instruments drawing 102–6518, dated Apr. 8, 1969.
Article entitled "Calibration and Use of the Aerodynamic Particle Sizer (APS 3300) by Paul A. Baron, published 1986.

Primary Examiner—Davis L. Willis
Assistant Examiner—Matthew W. Koren
Attorney, Agent, or Firm—Knobbe, Martens, Olson & Bear

[57] ABSTRACT

The sample air inlet nozzle into a particle counter test cell is formed with an elongated, flattened tip to provide a thin, flat laminar flow jet which intersects a laser beam. A secondary tube surrounding the nozzle provides a sheath of air which helps maintain the jet shape.

17 Claims, 1 Drawing Sheet

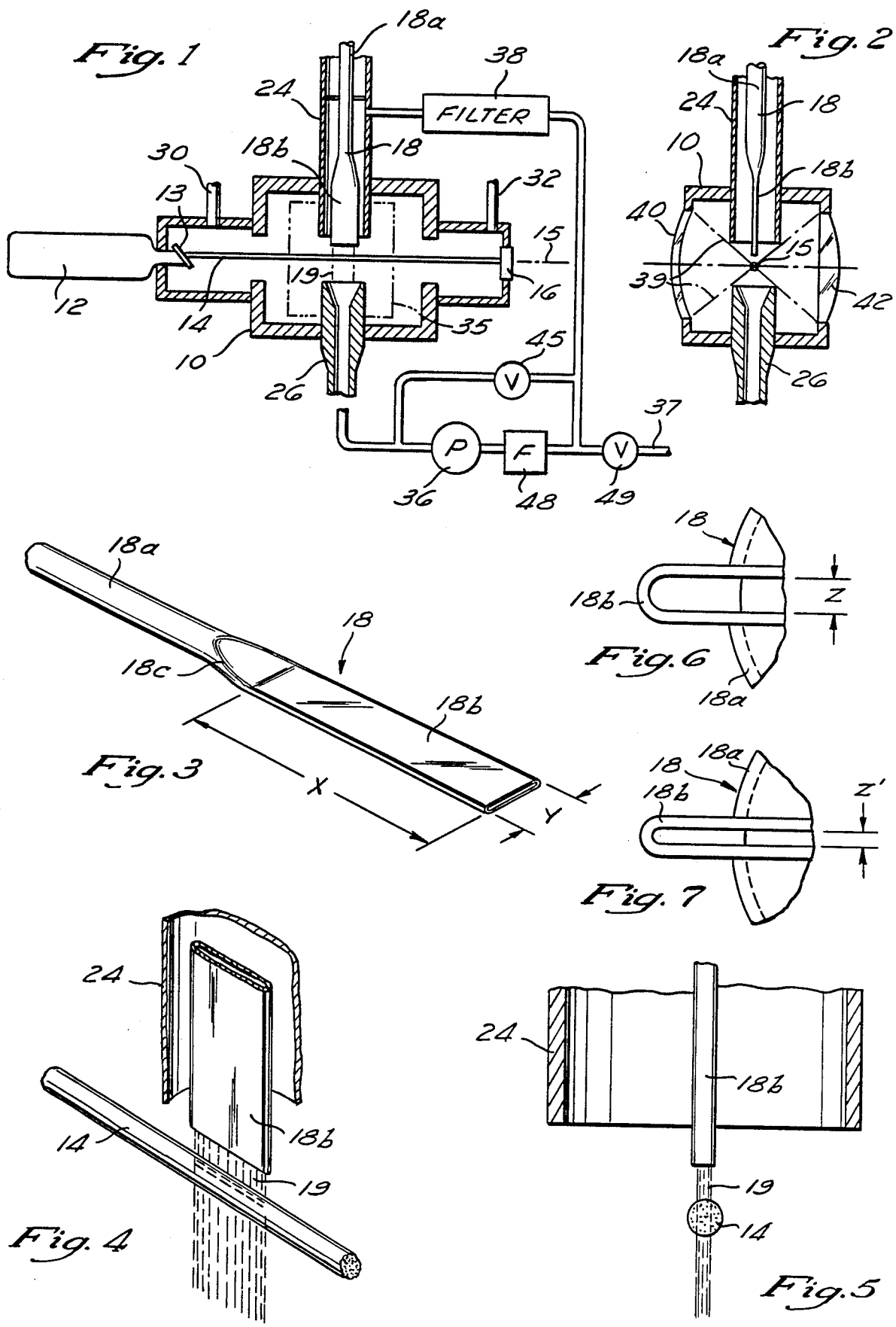

PARTICLE COUNTER AIR INLET ASSEMBLY

FIELD OF THE INVENTION

This invention relates to instruments for detecting, counting or otherwise measuring particles in fluids, particularly air. More specifically, the invention relates to an improved airflow system in such an instrument.

BACKGROUND OF THE INVENTION

Instruments for measuring particles in air are utilized in an increasing number of situations. Perhaps the single largest field of use is in the semiconductor industry wherein cleanliness in fabricating semiconductors is extremely important. For example, particle counters are utilized to monitor the number of particles in so called clean rooms in which semi-conductor manufacturing operations are conducted. Clean rooms are usually classified on the basis of the maximum number of particles of a given size permitted per volume of air. To meet specifications and maintain quality levels of the product being made, it is necessary to ensure that particle contamination is kept to an acceptable minimum requirement.

The basic system utilized in most airborne particle counters transmits a sample air stream through a beam of light, which results in light energy being scattered by the particles. This energy is detected and measured by suitable optics and electronics. Significant improvements have been made in the optics and electronics employed for detecting and processing the scattered light signals. Also, the advent of lasers has greatly improved the quality and intensity of the illuminating light beam.

In spite of these improvements, the accuracy of the data output from the instruments still leaves much to be desired. For example, in testing or calibrating particle counters, one technique employed is to inject a sample jet stream through the instrument that carries only particles of a known size. Output signals from such a test sample should be fairly uniform. However, it has been found that typically such results are not very uniform. Similar tests also reveal other inaccuracies, such as recirculating particles and appreciable discrepancies in absolute count correlation between different instruments. Thus, further improvements of particle counters are needed.

It is believed that one area of the instrument that has not received sufficient attention is the system for providing the sample air jet that flows into the instrument. One type of previously used nozzle is simply a tube with a circular cross section. Another type employs a tube with a circular cross section having a short tip with a generally rectangular cross section to fit within the diameter of the light beam. One nozzle of that type was made fairly precise by investment casting. In another arrangement, the end of a circular tube was pinched by a suitable tool to be less than the diameter of the light beam. A tube surrounding a nozzle for focusing or otherwise confining the jet has been used. These lack some uniformity of results. Thus, a need exists for improving the sample airflow delivery system.

SUMMARY OF THE INVENTION

Briefly stated, the present invention comprises a particle counter with an improved gas delivery system which provides a sample gas jet that consistently has a laminar and well defined flow as it passes through the sensing zone of the light beam. The laminar flow is desirable for a variety of reasons. In order to have an accurate instrumental evaluation, it is, of course, necessary that all of the particles in the sample flow through the light beam. Thus, it is necessary that the jet remain precise and well controlled as it passes through the beam. Secondly, turbulence in the sample jet boundary layer can cause recirculation of particles, which, of course, results in an inaccurate count. Recirculation can also contaminate mirrors or other optical elements in the test cell, resulting in errors in the readings and requiring frequent cleaning. Further, substantial turbulence in the jet flow can actually disturb the laser beam characteristics, and in fact can critically affect the laser power and stability in applications utilizing "open-cavity" laser resonators. The sample gas is introduced into the test cell of the instrument by means of a nozzle having an elongated tip with a flattened constant cross section. It has been found that such an elongated tip provides greatly improved results over previously used nozzle tips. Preferably, this flattened tip extends at least three times the longer dimension of the nozzle tip interior cross section or extends at least a half inch with a substantially constant cross section.

In addition to the use of an elongated flattened nozzle tip, the gas delivery system of the invention employs a separate tube surrounding the nozzle. Filtered gas flows through this tube to help confine the jet within its original boundaries without reducing or focusing effects.

DESCRIPTION OF THE DRAWINGS

FIG. 1 is a schematic view of a portion of a particle counter illustrating the invention;

FIG. 2 is a side elevational schematic view of the apparatus of FIG. 1;

FIG. 3 is a perspective view of the nozzle of FIGS. 1 and 2 illustrating the dimensions of the flattened tip;

FIG. 4 is an enlarged, perspective, schematic view of the nozzle tip within its co-flow tube, and with an air jet passing through a light beam.

FIG. 5 is an enlarged edge view of the nozzle and co-flow tube schematically illustrating the air jet of FIG. 4 passing through the light beam;

FIG. 6 is an enlarged fragmentary end view of the flattened tip of one size of the nozzle, showing an edge of the tip; and FIG. 7 is a view similar to FIG. 6 of a nozzle tip which is even thinner than that of FIG. 6.

DETAILED DESCRIPTION OF THE DRAWINGS

Referring to FIG. 1, there is schematically shown a portion of an optical particle counter utilizing an open-cavity laser design, including a main sensor cell body 10, laser plasma tube 12, and ancillary cavity end-mirror 16, which define the intracavity light beam axis 15 of the illuminating radiation 14.

An air inlet nozzle 18 introduces a jet of air 19 into the cell body 10, such air jet carrying particles to be detected. While the primary usefulness of this product is for evaluating particles within air, it will, of course, be understood that the instrument is useful in detecting particles in other gases as well. Since the dimensions and parameters given below concern airborne particles, it is possible that some changes in the instrument may be required for other gases, but the same principles are employed. The nozzle 18 directs the sample air jet 19 into the main sensor cell 10, at an angle of 90° with respect to the light beam 14, with the nozzle being situated so that the air jet 19 emanating from it will pass through the light beam. A control air duct 24 surrounds the nozzle and also extends into the main sensor cell body. A sample air exhaust nozzle 26 extends through the wall of the sensor cell body opposite of that of the inlet nozzle 18. A purge air inlet 30 is located adjacent one end of the laser plasma tube Brewster window 13 and a second purge air inlet 32 is located near the cavity end mirror 16.

Typically, the sensor cell 10 is sealed and sample air is introduced through the nozzle by means of a vacuum pump 36 connected to the sample exhaust 26. A portion of the air drawn in through the nozzle 18 and out through the exhaust 26 is recirculated through a filter 38 and into the control air duct 24 surrounding the nozzle 18. Also a portion of the filtered air is introduced to the two purge air inlets 30 and 32 which direct clean flows of air in a manner to prevent contaminates from engaging critical optical surfaces in the system. The purge air also exits from the cell through the sample exhaust 26. Sample air is passed through a filter 48 to an exhaust 37. The amount of air allowed to pass through the filter 38 is controlled by adjusting the valve 45 which is connected in parallel with the pump 36 to allow recirculation of a portion of the pump output. The valve 49 downstream from the pump 36 controls the sample gas flow rate.

Thus, in accordance with the general operation of an optical particle counter, the air to be sampled is introduced through the nozzle 18, intersects the light beam 14 and is exhausted through the sample exhaust 26. As the sample air jet is directed through the light beam, the particles in the beam scatter some of the light and these scattered light signals, schematically shown at 39 in FIG. 2, are collected by suitable detection means schematically illustrated by the broken line 35 in FIG. 1. As is typical for many light scattering sensors, the detection means is also centrally located at 90° with respect to the light beam axis 15, as indicated in FIGS. 1 and 2. Various forms of detection equipment are known to those skilled in the art and hence they are not described in detail herein. Also apparatus of this type is available from the assignee of this invention. A portion of the optics of such detection means is schematically illustrated in FIG. 2 by a mirror 40 on one side of the beam receiving signals 39, and a lens 42 receiving reflected signals from the mirror and receiving direct signals from the scattered light.

As indicated above, it is important that the sample air jet be precisely controlled so as to provide uniform, laminar flow with a consistent and precise cross section as the jet passes through the light beam. In accordance with the present invention, this is primarily accomplished by the unique geometry of the air inlet nozzle. The result is further enhanced by utilizing the nozzle in combination with the control air duct.

As seen in FIG. 3, the inlet nozzle 18 has an upstream tubular portion 18a with a circular cross section, and a downstream flattened tip 18b connected to the tubular portion 18a by a smoothly tapered transition section 1c. As may be seen from FIGS. 3 and 4, the flattened tubular tip has a generally rectangular cross section. The longer sides of the cross section are precisely parallel although the ends of the cross section are rounded, as seen in FIGS. 6 and 7. Thus, it might be said that the cross section has somewhat of an elongated racetrack cross section.

As seen from FIG. 4, the interior shorter dimension of the nozzle tip cross section is smaller than the diameter of the laser beam so that the entire air jet will pass through the beam. More specifically, the shorter dimension is less than or equal to about one half the beam diameter in two versions of the invention scheduled for production. The longer dimension of the tip cross section is selected to provide sufficient sample airflow at an acceptable velocity. Also, the longer dimension must be kept within the accuracy limits of the radiation detecting optics. These parameters determine the diameter of the tubular portion of the nozzle which is required to provide the needed tip portion, with the tip being formed by flattening the end of the tubular portion. As may be seen, the longer dimension of the nozzle tip cross section is much greater than the shorter dimension. In one form of the invention scheduled for production, the laser beam is about 0.06 inch diameter. The nozzle tip to be used with that laser is illustrated in FIG. 6 and has a shorter interior dimension z of about 0.03 inch, while the longer interior dimension y is 0.45 inch. Thus, the longer dimension is about fifteen times greater than the shorter dimension. In another form of the invention, the laser beam has a diameter of about 0.02 inch, and the lower flow nozzle to be used with it, shown in FIG. 7, has an interior shorter dimension z' of only about 0.01 inch, such that the longer dimension y is about 45 times greater. From these examples, the extreme thin, flat nature of the air jet emanating from the nozzle can be appreciated.

The entire flattened tip of the nozzle up to the transition section 18c has a constant cross section. In the high volume flow form of the invention in FIG. 6, this dimension x is approximately 2.25 inches. In a version of the nozzle shown in FIG. 7, this dimension x is 1.5 inches. Thus, it can be stated that in one form of the invention, the length of the constant cross section flattened tip portion is about five times greater than the longer dimension of the nozzle tip cross section, and about three times greater than the nozzle tip cross section in the second mentioned form of the invention.

In the forms of the invention shown in FIGS. 6 and 7, the nozzle tubular portions 18a have a circular cross section of about 0.29 inch. Since this diameter is related to the longer dimension of the nozzle tip cross section, it may also be meaningful to state that the length of the flattened tip portion 18b is almost eight times greater than the inner diameter in one form of the invention and more than five times greater than the tube inner diameter in the other form mentioned. Thinness of the jet is also important from a standpoint of laminar flow. Relating the axial length of the constant cross section of the tip to the shorter dimension of the tip, it can be stated that, in the FIG. 6 form of the invention, the 2.25 inch length is about 75 times greater than the shorter dimension. In the form of the invention shown in FIG. 7, the 1.5 inch length is about 150 times greater than the 0.01 inch shorter interior dimension of the tip cross section. Preferably, the length of the flattened tip is at least 50 times greater than the shorter dimension of the jet. Thus, again, the flat laminar flow of the resulting jet can be appreciated.

The necessary length of the flattened tip is related to the flow rate through the nozzle, a longer tip being required for higher flow rates to obtain the desired laminar flow. Increasing the length of the flattened portion 18b improves the laminar flow of the air jet. However, there is, of course, an offsetting pressure drop accompanying an increase in the length. Also, increasing the length increases the difficulty of making the nozzle with the desired precision. It is believed that the flattened tip length should be at least 0.5 inch to obtain the desired laminar flow with lower flow rates, and greater than that for higher flow rates.

As indicated above, the shorter dimension of the tip cross section is dictated by the laser beam diameter. Providing a laser beam of increased diameter would require less flattening of the tube such that an adequate airflow could possibly be obtained with a smaller diameter tube with circular cross section. However, increasing intracavity laser beam diameter represents a substantial complexity regarding instrument sensitivity, laser resonator design, and coordination with the associated optics and electronics. In general, smaller beam diameters are desirable from a standpoint of beam power density, and are required in high-sensitivity instruments.

The control air duct further enhances stability and consistency of the laminar nature of the air jet. The control air moves at a velocity considerably less than the sample air jet. The control air serves as a curtain or sheath of air surrounding the faster moving jet. This sheath tends to confine and resist movement of the air jet out of its laminar flow pattern. It should be noted, however, that the control air sheath does not restrict the cross section of the air jet. That is, it does not perform an aerodynamic focusing function, but merely a confining function as it inhibits excessive entrainment and mixing of the sample jet and surrounding medium. Since the control air has been filtered, such air sheath does not add further particles to the sample air, even if there should be some slight mixing at a point further downstream from the exit of the nozzle.

From the standpoint of maximizing scattered light signal strength, it is desirable to use a thin nozzle to minimize light obstruction. A thin wall also helps maintain laminar jet flow by minimizing turbulence at the tip outlet. In the forms of the invention referred to above, the wall thickness is about 0.01 inch. The use of thin wall material also insures a thin, uniform tip edge that aids laminar jet flow and flow stability.

It is also important that the nozzle air jet forming surfaces be formed to foster laminar flow. Thus, preferably, the inside surface of the nozzle has a smooth, almost reflective finish.

Since the thrust of the invention is to obtain uniform, laminar air jet flow through the light beam, it is desirable to position the end of the nozzle flat portion 18b close to the beam, but at the same time, the nozzle and the flow tube 24 should not appreciably block scattered light signals or introduce additional stray light levels that could adversely affect the sensitivity or accuracy of the readings obtained. In the arrangement of FIGS. 4 and 5, which illustrates the beams of about 0.06 diameter, the tip of the nozzle is about ⅛ inch from the center of the beam. Note that the nozzle extends slightly closer to the beam than does the co-flow tube 24.

Another parameter of a practical particle counter is that sufficient sample flow volume must be provided to obtain rapid readings. With the larger cross sectional area of the nozzle of FIG. 6, a flow can be obtained of up to one cubic foot per minute, which is considered high flow. The nozzle of FIG. 7 is projected to provide about 0.1 cubic foot per minute, which is considered moderate flow. The more accurate and sensitive particle counters (e.g., aerosol spectrometers) typically have low flow rates, in the range of 0.01 cubic foot per minute. With the nozzle of the present invention, high flow rates with low turbulence are provided, thus increasing accuracy, sensitivity, and more statistically significant readings.

What is claimed is:

1. An instrument for analyzing and counting particles in air or other gas, comprising a system for transmitting a jet of gas through a concentrated light beam in a test cell so as to illuminate the jet and cause light to be scattered by particles in the jet, said system including a gas inlet nozzle forming and directing the jet into the test cell, said nozzle having a flattened, thin walled tip portion with a generally rectangular interior cross section that produces a thin flat jet in which the longer dimension of the cross section of the jet is much greater than the shorter dimension, and the length of said nozzle flattened portion is at least three times greater than said cross section longer dimension, with the result being that the jet formed by the nozzle has very laminar flow as it passes through said beam.

2. The instrument of claim 1 wherein said nozzle has an upstream tubular portion of circular cross section joined to said flattened tip portion by a very smoothly tapered transition portion.

3. The instrument of claim 2 wherein said flattened portion is formed by flattening the end of the tubular portion.

4. The instrument of claim 1 wherein the shorter dimension of said jet cross section is less than or approximately equal to half the cross sectional dimension of the light beam through which the jet passes.

5. The instrument of claims 1, 2, 3 or 4 including a duct surrounding and spaced outwardly from said nozzle to conduct a sheath of air surrounding the jet and the nozzle so as to help confine the jet and resist the creation of turbulence.

6. The instrument of claim 5 wherein said nozzle tip extends slightly beyond the end of said duct.

7. The instrument of claim 1 wherein the longer dimension of the jet cross section is more than 10 times greater than the shorter dimension.

8. The instrument of claim 1 wherein the length of said flattened tip portion is at least 0.5 inch.

9. A particle counter comprising:
   means forming a test cell for illuminating and detecting particles in a gas stream;
   means providing a high intensity light beam passing through the test cell;
   means for introducing a sample jet of gas transversely through the light beam; and
   means for detecting and measuring light scattered from particles carried by the jet and illuminated by the light beam;
   said jet introducing means, including an inlet nozzle having a thin wall tubular portion which tapers smoothly to an elongated, flattened tip portion having a constant cross section which causes the jet to have a corresponding flattened, generally rectangular cross section with the shorter dimension of the cross section extending perpendicular to the light beam optical axis and being less than the diameter of the light beam, and with the longer dimension of the jet cross section extending in the direction of the light beam, the axial length of said flattened tip portion extends at least 0.5 inch, whereby the jet has an extremely laminar flow.

10. The instrument of claim 9 wherein the wall thickness of said nozzle is about 0.01 inch.

11. The instrument of claim 9 wherein the interior surface of said tube and tip portion is extremely smooth and free of blemishes that might cause turbulence in the air jet.

12. The instrument of claim 9 wherein the axial length of said flattened tip is more than 50 times greater than the shorter dimension of said jet.

13. The instrument of claim 9 wherein the axial length of said flattened tip is approximately 2.25 inches.

14. The instrument of claim 13 wherein the shorter dimension of said tip cross section is about 0.03 inch.

15. The instrument of claim 9 wherein the axial length of said flattened tip is approximately 1.5 inches.

16. The instrument of claim 15 wherein the shorter dimension of said tip cross section is approximately 0.01 inch.

17. The instrument of claim 9 including a gas outlet nozzle in said cell, a duct surrounding and spaced from said inlet nozzle, a pump connected to said outlet nozzle and to an exhaust line, to draw sample gas flow into said cell through said inlet nozzle, a valve in said line to control the inlet gas flow, a conduit recirculating a portion of the pump output to said duct so that a sheath of gas flows into said cell around said jet, a conduit connected in parallel to said pump with a valve in said conduit whereby a portion of the pump output is recirculated to the pump inlet to thereby control the flow through said duct, and a particle filter for filtering particles from the gas fed to said duct.

* * * * *